United States Patent [19]

Steinkohl

[11] Patent Number: 4,761,135
[45] Date of Patent: Aug. 2, 1988

[54] BAND CARRIER FOR ORTHODONTIC BANDS

[76] Inventor: Hannelore Steinkohl, Gutenbergstrasse 11, D-8950 Kaufbeuren, Fed. Rep. of Germany

[21] Appl. No.: 20,554

[22] Filed: Mar. 2, 1987

[30] Foreign Application Priority Data

Mar. 20, 1986 [DE] Fed. Rep. of Germany ....... 3609474

[51] Int. Cl.⁴ .............................................. A61C 19/02
[52] U.S. Cl. ........................................ 433/49; 433/23; 433/72
[58] Field of Search ....................... 433/49, 23, 24, 25, 433/50, 51, 72, 229; 434/263

[56] References Cited

U.S. PATENT DOCUMENTS

| | | | |
|---|---|---|---|
| 1,458,782 | 6/1923 | Shapiro | 433/263 |
| 2,545,249 | 3/1951 | Ackerman | 433/72 |
| 4,014,096 | 3/1977 | Dellinger | 433/24 |

OTHER PUBLICATIONS

"The Design and Construction of Removable Orthodontic Appliances", by C. Philip Adams, 4th edition, 1970, p. 41, Unitek, catalog 118, 1978, pp. 2 and 3.

Primary Examiner—John J. Wilson
Attorney, Agent, or Firm—Toren, McGeady & Associates

[57] ABSTRACT

For orthodontists a band carrier assembly for orthodontic bands is provided which consists of a carrier plate with an arrangement of pins on to which the bands may be fitted.

11 Claims, 1 Drawing Sheet

BAND CARRIER FOR ORTHODONTIC BANDS

BACKGROUND TO THE INVENTION

The invention relates to a band carrier for orthodontic bands.

In orthodontics as a rule the following procedure is adopted:

A selection of bands, that is band-type rings of different diameters, is available. For the production of a dental correction apparatus firstly bands fitting the individual teeth are selected and each is adapted to the respective tooth. Then the bands thus adapted are placed in order corresponding to the allocation to the teeth. Next the bands are partly coated with covering wax and disinfected. Finally the bands are filled with cement and fitted each on to its respective tooth. After the fitting of the bands they are connected by wires to form a correcting apparatus.

OBJECT OF THE INVENTION

An object of the invention is to provide the placement of the selected bands, adapted each to its tooth, ready for subsequent installation on a set of teeth, in a clearly laid-out and ergonomically favorble manner.

SUMMARY OF THE INVENTION

According to the invention a band carrier assembly for orthodontic bands is provided which comprises a carrier plate with an arrangement of pins onto which the bands can be set. The dentofacial orthodontist can then fit the selected bands on to pins allocated to the individual teeth and thus, in the subsequent fitting, recognise the association of the individual bands with the individual teeth by reference to the association of the pins with the individual teeth.

By way of example the orthodontist can proceed as follows:

From his collection of bands of different diameters he takes an approximately fitting band for each individual tooth and further adapts this band to the tooth concerned, by mechanical deformation. The bands thus adapted are then set on to the pins associated with the respective teeth. Next he provides the bands in succession with wax coating in those zones where no cement is to adere, and after wax coating has taken place he sets the bands back each on to its pin. Thereupon the bands are disinfected, for example by dipping of the carrier plate with all the bands into a disinfecting solution such as alcohol. Next the bands arranged in rows on the pins can be dried by blowing with air. Now installation commences. For this purpose the bands are successively filled with cement and each pushed over the tooth concerned. In taking up the bands for subsequent fitting the orthodontist can be guided by the allocation of the pins receiving the respective bands to the individual teeth.

In order to facilitate the handling of the bands, and especially their fitting on to and removal from the fit-on pins, these are preferredly made with a diameter which permits radial play of the bands. It is further advisable to arrange the pins at such distance from one another that the bands fitted on adjacent pins remain out of mutual contact.

The number of the pins on the carrier plate should be at least and preferably equal to the number of teeth of a jaw, that is the upper jaw or the lower jaw. Since corrections have frequently to be effected both to the upper jaw and to the lower jaw at the same time, the number of pins is preferably made equal to the number of teeth of the upper jaw and the lower jaw.

The allocation of the individual pins can be made recognizable by any desired aids, for example by inscriptions for the individual pins. However the pins are preferably provided along an arc corresponding to the band from the position in each case of the pin carrying it, within the arc. It is here conceivable perhaps to distinguish the pins for the bands allocated to the front incisors by different shaping or coloration, since as a rule the fitting of the bands starts from there. In order to associate the bands for the upper jaw and those for the lower jaw logically with one another, it is advisable to arrange the pins along two approximately mutually parallel arcs which correspond to the arcuate courses of upper and lower jaws. Here the arc with the larger radius of curvature corresponds to the upper jaw and the arc with the smaller radius of curvature corresponds to the lower jaw, in accordance with the difference of curvatures of upper jaw and lower jaw. The individual pins of the two arcs can here be logically associated with one another in such manner that the pins for the bands of mutually associated teeth of the upper and lower jaws stand opposite to one another transversely of the arcuate lines.

For aesthetic and hygienic reasons it is advisable that the carrier plate should consist of transparent material, especially transparent synthetic plastics material.

In order to achieve simple securing of the carrier pins on the carrier plate, these can be inserted into bores of the carrier plate and riveted fast. The pins consist for example of stainless steel.

In order that the individual band carrier may be grasped easily, for example for dipping into disinfectant solution, it is advisable to provide the carrier plate with feet.

BRIEF DESCRIPTION OF THE DRAWINGS

In the accompanying drawings.

DESCRIPTION OF PREFERRED EMBODIMENT(S)

Figure 2:
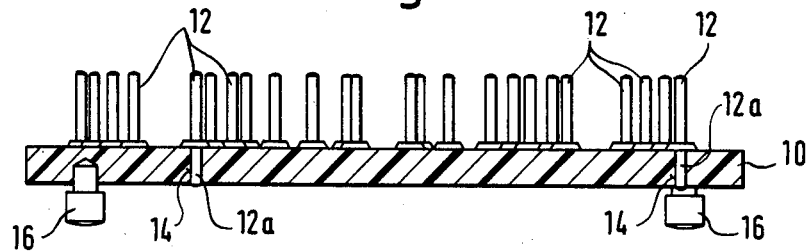
FIG. 2 represents a section along line II—II in FIG. 1.
Figure 1:
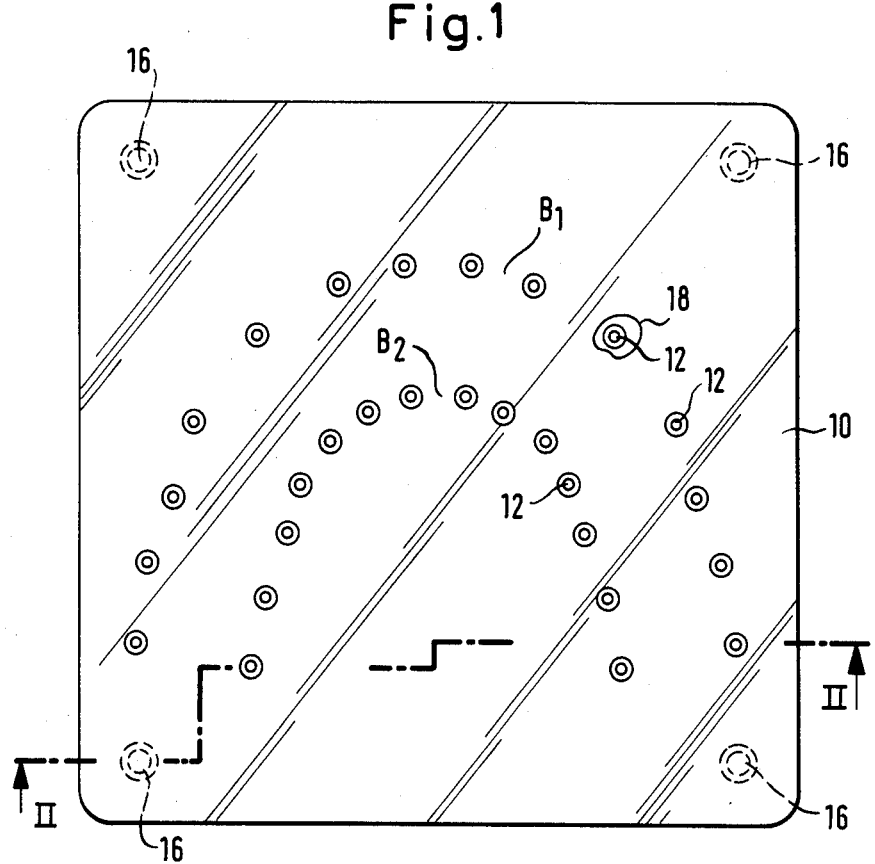
FIG. 1 represents a plan view of a band carrier according to the invention.

A band carrier according to FIGS. 1 and 2 consists of an acrylic transparent panel 10 having a plurality of pins 12 for the reception of bands. The pins 12 are pressed with a securing shank 12a into securing bores 14 formed in the carrier plate 10, and may be made fast by riveting. The carrier plate 10 is provided with feet 16 for standing.

In FIG. 1 it is seen that the pins 12 are arranged along two arcs $B_1$ and $B_2$, the arc $B_1$ corresponding to the upper jaw and the arc $B_2$ to the lower jaw. In each case a pin 12 of the arc $B_1$ stands opposite to a pin 12 of the arc $B_2$. In FIG. 1 there is seen a band 18 which is fitted on to a pin 12 and is already adapted to a tooth.

It is seen that the bands 18 with the carrier plate 10 can be dipped into disinfectant soluton. Likewise it is seen that it is an easy thing to dry the bands after dipping, by conducting a blown jet of hot air over the plate 10.

I claim:

1. A band carrier assembly for supporting orthodontic bands comprising:

(a) a carrier plate, and (b) a plurality of pins extending from at least one major surface of the plate for receiving said bands, said pins being arranged in an array commensurate with a jaw, the pins being arranged along two mutually approximately parallel arcs which correspond to the arcuate form of upper jaw and lower jaw.

2. A band carrier assembly according to claim 1, including bands provided on at least some of the said pins, said pins having a diameter which permits a play of the respective band radially with respect to the pins.

3. A band carrier assembly according to claim 2, wherein the pins are arranged at such distance from one another that the bands fitted on to adjacent pins remain out of mutual contact.

4. A band carrier assembly according to claim 1, wherein the number of pins in a first arc is at least equal to the number of teeth of a lower jaw and the number of the pins in a second arc is at least equal to the number of teeth of an upper jaw.

5. A band carrier assembly according to claim 1, wherein the pins for receiving the bands for adjacent teeth of the upper jaw and of the lower jaw are adjacent to one another on the carrier plate.

6. A band carrier assembly according to claim 1, wherein the carrier plate consists of transparent material.

7. A band carrier assembly according to claim 1, wherein the pins are received in bores of the carrier plate and are secured by pressure fit.

8. A band carrier assembly according to claim 1, wherein the pins are received in bores of the carrier plate and are secured by riveting.

9. A band carrier assembly according to claim 1, wherein the pins consists of stainless steel.

10. A band carrier assembly according to claim 1, wherein the carrier has plate has feet.

11. A band carrier assembly according to claim 1, wherein the carrier plate possesses an approximately square outline.

* * * * *